United States Patent [19]

Miller et al.

[11] Patent Number: 5,599,990
[45] Date of Patent: Feb. 4, 1997

[54] PROCESS FOR PREPARING QUATERNARY AMMONIUM COMPOUNDS

[75] Inventors: Joseph H. Miller; Joe D. Sauer; Dru L. DeLaet, all of Baton Rouge, La.

[73] Assignee: Albemarle Corporation, Richmond, Va.

[21] Appl. No.: 548,991

[22] Filed: Oct. 27, 1995

Related U.S. Application Data

[63] Continuation-in-part of Ser. No. 407,828, Mar. 21, 1995, abandoned.

[51] Int. Cl.$^6$ .................... C07C 209/12; C07C 211/62; C07C 211/63; C07C 211/64
[52] U.S. Cl. .................... 564/296; 549/513; 556/413; 556/425; 558/27; 558/452; 560/142; 560/155; 560/196; 560/250; 564/282
[58] Field of Search .................... 564/296, 282; 549/513; 556/413, 425; 558/27, 452; 560/142, 155, 196, 250

[56] References Cited

U.S. PATENT DOCUMENTS

| 4,228,096 | 10/1980 | Bozzelli et al. | 558/28 |
| 4,883,917 | 11/1989 | Smith et al. | 564/292 |
| 5,196,582 | 3/1993 | Smith et al. | 564/296 |
| 5,463,094 | 10/1995 | Brown et al. | 564/296 |

FOREIGN PATENT DOCUMENTS

| 0288857 | 11/1988 | European Pat. Off. | 564/296 |
| 56940 | 4/1985 | Japan | 564/296 |
| 1144217 | 3/1969 | United Kingdom | 564/296 |

*Primary Examiner*—Joseph E. Evans
*Attorney, Agent, or Firm*—Philip M. Pippenger

[57] ABSTRACT

A quaternary ammonium halide is prepared by reacting a substituted or unsubstituted haloalkane with a tert-amine in a mol ratio not higher than 1.1/1 in the absence of a solvent and at a temperature such as to maintain the reaction mixture liquid.

11 Claims, No Drawings

PROCESS FOR PREPARING QUATERNARY AMMONIUM COMPOUNDS

CROSS-REFERENCE TO RELATED APPLICATION

This application is a continuation-in-part of application Ser. No. 08/407,828, filed Mar. 21, 1995, now abandoned.

FIELD OF INVENTION

The invention relates to a process for preparing quaternary ammonium compounds.

BACKGROUND

As is known, quaternary ammonium compounds (also known as "quats") have utility in various applications (e.g., as fungicides, algicides, bactericides, and bleach activators) and can be prepared by reacting tert-amines with suitable quaternizing agents. Different types of materials have been used as quaternizing agents in such reactions, but haloalkanes are apt to be preferred.

Known quaternizations of tert-amines have typically been conducted in organic solvents which must be separated from the product at the end of the reaction, thus increasing costs. European Patent Application 0288857 (Rutzen et al.) shows that the necessity of recovering product from a solvent can be avoided when a tert-amine is quaternized under pressure with an excess of an alkyl halide that is gaseous under the reaction conditions. However, this process has the disadvantages of requiring the recovery, recycling, or disposal of the excess alkyl halide, as well as the use of pressure equipment; and it is not suitable for the preparation of quats in which the quaternizing group has a relatively long chain.

SUMMARY OF INVENTION

It has now been found that the disadvantages of known quaternization processes can be avoided when a quaternary ammonium compound is prepared by reacting a substituted or unsubstituted haloalkane with a tert-amine in a mol ratio not higher than 1.1/1 in the absence of a solvent and at a temperature such as to maintain the reaction mixture liquid.

DETAILED DESCRIPTION

The tert-amine employed in the practice of the invention may be any tert-amine that it might be desirable to quaternize. However, because of the greater interest in the quats prepared from them, the preferred tert-amines are apt to be those corresponding to the formula RR'R"N in which R is an alkyl group containing 4–24 carbons; R' is methyl, ethyl, or —$(CH_2CH_2O)_nH$ in which n is 1–20; and R" is independently selected from methyl, ethyl, —$(CH_2CH_2O)_nH$, and alkyl groups containing 4–24 carbons.

More preferably, the tert-amine is a compound corresponding to the above formula in which R is an alkyl of 6–20 carbons; R' is methyl, ethyl, or 2-hydroxyethyl; and R" is independently selected from methyl, ethyl, 2-hydroxyethyl, and alkyls of 6–20 carbons. The most preferred tert-amines are the compounds wherein R is an alkyl of 8–18 carbons and both R' and R" are methyl.

Exemplary of these preferred tert-amines are the N-butyl-, N-hexyl-, N-octyl-, N-decyl-, N-dodecyl-, N-tetradecyl-, N-hexadecyl-, N-octadecyl-, N-eicosyl-, N-docosyl-, and N-tetracosyl-N,N-dimethylamines; the corresponding N-alkyl-N,N-diethylamines; the corresponding N-alkyl-N, N-di-2-hydroxyethylamines; the corresponding N-alkyl-N, N-di(ethoxylated hydroxyethyl)amines wherein the ethoxylated hydroxyethyl groups correspond to the formula —$(CH_2CH_2O)_mH$ in which m is 2–20, preferably 2–10; the corresponding N-alkyl-N-methylethylamines; the corresponding N-alkyl-N-methyl-2-hydroxyethylamines; and the corresponding N,N-dialkylmethyl-, N,N-dialkylethyl-, and N,N-dialkyl-2-hydroxyethylamines, including mixtures thereof.

The substituted or unsubstituted haloalkane with which the tert-amine is reacted is a compound which is normally liquid or can be rendered liquid at elevated temperatures and ambient pressure and which is usually a chloro- or bromoalkane, preferably a bromoalkane. Since the invention is of particular value in the preparation from N-alkyldimethylamines of quats containing two long-chain alkyl groups, the quaternizing agents preferred for reaction with the most preferred tert-amines are unsubstituted chloro- or bromoalkanes containing 4–24, more preferably 6–20, and most preferably 8–18 carbons—the number of carbons being the same as or different from the number of carbons in the long-chain alkyl group of the tert-amine. However, in the preparation of other quats, it is sometimes preferred to employ a substituted haloalkane in which the substituent is a group that it is desired to have in the quat product. For example, a halomethane bearing a phenyl or alkylphenyl substitutent is used when a benzyl- or alkylbenzyl quaternizing group is the goal; and functional groups can be introduced by the use of the substituted haloalkane quaternizing agents taught in U.S. Pat. No. 4,883,917 (Smith et al. ), the teachings of which are incorporated herein by reference. Mixtures of haloalkane compounds can also be used if desired.

The quaternization process is conducted by mixing the reactants in the absence of a solvent and maintaining the solvent-free reaction mixture at a temperature such as to keep it liquid and stirrable until the desired product has been formed. To avoid the recovery, disposal, and/or recycling problems associated with known processes for preparing the quats, it is important to combine the quaternizing agent and tert-amine in a mol ratio not higher than 1.1/1; and it has been found that high conversions can be obtained when the ratio is about 0.8–1.1/1, preferably about 1/1. The temperature and time required for the reaction are interdependent and also influenced by other factors, such as the molecular weights of the particular reactants employed, but are generally in the ranges of about 25°–250° C. and about 5 minutes to 5 days.

The invention is advantageous in that it provides a method of preparing quats without the use of any solvent or excess quaternizing agent that would require the utilization of separation, disposal, or recycling steps and without the need for pressure equipment. As already taught, this more economical process can also be used in the production of other quats but is particularly valuable in the preparation of quats having two methyls and two long-chain alkyls attached to the nitrogen—compounds that have conventionally been prepared by reacting a halomethane with a dialkylmethylamine. The alkyldimethylamines that can be employed to prepare such quats in accordance with the present invention are less expensive to prepare than dialkylmethylamines, so the ability to use them adds to the economy of the process.

The following examples are given to illustrate the invention and are not intended as a limitation thereof.

EXAMPLE 1

Charge a suitable reaction vessel with 450.0 g (1.9 mols) of N-tetradecyl-N,N-dimethylamine and heat it to 105° C.

under nitrogen. After maintaining that temperature for 15 minutes, add 309.5 g (1.9 mols) of bromohexane to effect an exotherm that raises the temperature to 115° C. Hold the temperature at 115° C. for 8 hours, take a sample for analysis, maintain the 115° C. temperature for an additional 11 hours, raise it to 120° C., and then quickly transfer the reactor contents while still hot and fluid. Wet chemical analysis shows the final product to contain 97.3% N-tetradecyl-N-hexyl-N,N-dimethylammonium bromide, 1.2% of the corresponding amine hydrobromide, and 0.5% free amine. Analysis of the sample taken at 8-hours reaction time shows the reaction to have been essentially complete at that time— 1.12% amine hydrobromide and 0.58% free amine.

EXAMPLE 2

Charge a suitable reaction vessel with 400.0 g (1.9 mols) of N-dodecyl-N,N-dimethylamine and heat it to 105° C. under nitrogen. Add 363.5 g ( 1.9 mols) of bromooctane to effect an exotherm that raises the temperature to 125° C. Then heat the reaction mixture at 130° C. for 17 hours and transfer the reaction mass from the reactor while still hot and fluid. Wet chemical analysis shows the product to contain 93.7% N-octyl-N-dodecyl-N,N-dimethylammonium bromide, 4.1% of the corresponding amine hydrobromide, and 0.5% free amine.

EXAMPLE 3

Charge a suitable reaction vessel with 343.1 g (1.8 mols) of N-decyl-N,N-dimethylamine and heat it to 110° C. under nitrogen. Add 406.9 ( 1.8 mols) of bromodecane to effect an exotherm that raises the temperature to 140° C., then hold the temperature at 110° C. for 12 hours, and transfer the reaction mass from the reactor while still hot and fluid. Wet chemical analysis shows the product to contain 90% N,N-didecyl-N,N-dimethylammonium bromide, 4.3% of the corresponding amine hydrobromide, and 0.33% free amine.

COMPARATIVE EXAMPLE

Charge a suitable reaction vessel with 421.2 g (2.3 mols) of N-decyl-N,N-dimethylamine and heat it to 110° C. under nitrogen. Add 499.7 g (2.3 mols) of bromodecane to effect an exotherm that raises the temperature to 130° C. Then add 115.1 g of water and 115.1 g of alcohol as solvents, hold the reaction temperature at 90° C. for 14 hours, and transfer the reaction mass from the reactor while still hot. Wet chemical analysis shows the product to contain 71.3% N,N-didecyl-N,N-dimethylammonium bromide, 1.78% of the corresponding amine hydrobromide, and 0.2% free amine.

What is claimed is:

1. In a process for preparing a quaternary ammonium halide by reacting a substituted or unsubstituted haloalkane with a tert-amine, the improvement which comprises reacting the haloalkane compound and tert-amine in a tool ratio not higher than 1.1/1 in the absence of a solvent and at a temperature such as to maintain the reaction mixture liquid.

2. The process of claim 1 wherein the tert-amine is a compound corresponding to the formula RR'R"N in which R is an alkyl group containing 4–24 carbons; R' is methyl, ethyl, or —$(CH_2CH_2O)_n$H in which n is 1–20; and R" is independently selected from methyl, ethyl, —$(CH_2CH_2O)_n$H, and alkyl groups containing 4–24 carbons.

3. The process of claim 2 wherein R is an alkyl of 6–20 carbons; R' is methyl, ethyl, or 2-hydroxyethyl; and R" is independently selected from methyl, ethyl, 2-hydroxyethyl, and alkyls of 6–20 carbons.

4. The process of claim 3 wherein R is an alkyl of 8–18 carbons and both R' and R" are methyl.

5. The process of claim 1 wherein the haloalkane compound is a bromoalkane compound.

6. The process of claim 5 wherein the bromoalkane compound is a bromoalkane containing 4–24 carbons.

7. The process of claim 6 wherein the bromoalkane contains 6–20 carbons.

8. The process of claim 7 wherein the bromoalkane contains 8–18 carbons.

9. The process of claim 4 wherein a tert-amine corresponding to the formula R$(CH_3)_2$N in which R is an alkyl of 8–18 carbons is reacted with a bromoalkane containing 6–20 carbons.

10. The process of claim 9 wherein the bromoalkane contains 8–18 carbons.

11. The process of claim 1 wherein the reaction is conducted at a temperature in the range of about 25°–250° C.

* * * * *

UNITED STATES PATENT AND TRADEMARK OFFICE
CERTIFICATE OF CORRECTION

PATENT NO. : 5,599,990
DATED : February 4, 1997
INVENTOR(S) : Joseph H. Miller; Joe D. Sauer; and Dru L. DeLaet It is certified that error appears in the above-indentified patent and that said Letters Patent is hereby corrected as shown below:

**Column 4, Line 10, reads "tool" and should read --mol--.
Compare claim 1, page 6, line 3.**

Signed and Sealed this

Fifteenth Day of June, 1999

Attest:

Q. TODD DICKINSON

*Attesting Officer*   *Acting Commissioner of Patents and Trademarks*